United States Patent [19]

Rollick et al.

[11] Patent Number: 5,019,611
[45] Date of Patent: May 28, 1991

[54] NON-STAINING AND SLIGHTLY-STAINING ANTIOZONANTS

[75] Inventors: Kevin L. Rollick, Munroe Falls; James G. Gillick, Akron; Joseph A. Kuczkowski, Munroe Falls, all of Ohio

[73] Assignee: The Goodyear Tire & Rubber Company, Akron, Ohio

[21] Appl. No.: 3,520

[22] Filed: Jan. 15, 1987

[51] Int. Cl.$^5$ .................. C08K 5/46; C07D 251/00
[52] U.S. Cl. .............................. 524/83; 524/96; 524/97; 544/8; 544/67; 544/180; 544/216; 544/220
[58] Field of Search .................. 524/100, 83, 96, 97; 544/8, 67, 180, 216, 220

[56] References Cited

U.S. PATENT DOCUMENTS

| | | | |
|---|---|---|---|
| 2,723,969 | 11/1955 | Naylor | 525/348 |
| 2,804,447 | 8/1957 | Naylor | 525/348 |
| 3,347,677 | 10/1967 | Jaworski et al. | 426/545 |
| 3,462,368 | 8/1969 | Wollensak et al. | 524/201 |
| 3,510,460 | 5/1970 | Fike | 525/281 |
| 3,632,631 | 1/1972 | Wright | 560/133 |
| 3,867,359 | 2/1975 | Beadle | 525/352 |
| 4,617,333 | 10/1986 | Costanzi et al. | 524/96 |

FOREIGN PATENT DOCUMENTS

| | | | |
|---|---|---|---|
| 120411 | 10/1984 | European Pat. Off. | 524/100 |
| 0278890 | 8/1988 | European Pat. Off. | 524/96 |
| 55750 | 5/1974 | Japan | 524/100 |
| 47406 | 6/1974 | Japan | 524/100 |
| 55346 | 5/1976 | Japan | 524/100 |
| 194933 | 11/1983 | Japan | 524/100 |
| 060819 | 5/1978 | U.S.S.R. | 524/100 |
| 887174 | 8/1970 | United Kingdom . | |

OTHER PUBLICATIONS

Chemical Abstracts 85:62535a.
Chemical Abstracts 85:62548y.
Verbilov, *Comparative Toxicological Characteristics of New Rubber Vulcanization Accelerators Triazinthion and Bio-Triazine* (1974).
Watanabe et al., J. Soc. Rubber Ind., Japan 41,664 (1968).

Primary Examiner—Kriellion Morgan
Attorney, Agent, or Firm—Marc R. Dion, Sr.

[57] ABSTRACT

There is disclosed compounds having, within their structural formulae, a trivalent moiety:

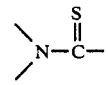

which exhibit antiozonant activity when added to rubber compositions at antiozonant effective levels and which exhibit synergistic antiozonant activity when used with conventional antiozonants in rubber compositions. There is also disclosed novel compounds which can be used as antiozonants.

28 Claims, No Drawings

NON-STAINING AND SLIGHTLY-STAINING ANTIOZONANTS

FIELD OF THE INVENTION

This invention relates to compounds having, within their structural formulae, a trivalent moiety:

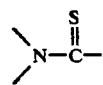

It relates to compounds which exhibit antiozonant activity when added to rubber compositions at antiozonant effective levels. It also relates to compounds which exhibit synergistic antiozonant activity when used with conventional antiozonants in rubber compositions. It also relates to novel compounds which can be used as antiozonants.

BACKGROUND ART

Essentially all types of rubber, both natural and synthetic, and particularly rubbers formed from dienes are known to be susceptible to deterioration resulting from prolonged exposure to ozone. A great deal of effort has been expended by those engaged in the field of polymer technology to develop various antiozonants that will effectively inhibit the adverse effects of ozone on polymeric compositions. The more commercially available antiozonants for rubber and rubber goods are the several derivatives of para-phenylenediamine. These derivatives generally suffer from one or more of the following limitations: limited solubility in rubber; low but significant volatility and water solubility: reactivity toward other species such as dioxygen; staining and discoloration. One approach to decreasing the water solubility and volatility of these derivatives of para-phenylenediamine has been to increase their molecular weight.

As a class, the para-phenylenediamine derivatives are very active antiozonants but their usefulness is greatly limited by their severe staining and discoloring nature. Thus considerable effort has been expended in the search for non-staining, non-discoloring antiozonants. Many materials have been investigated for this purpose including lactams, phosphites, phosphines, thioureas, thiosemicarbazides and substituted olefins but all have significant drawbacks and limitations. The lactams which are reported to have excellent dynamic ozone protection are very scorchy. Phosphites and phosphines react readily with peroxide and sulfur curatives and so are not useful in conventionally cured goods. Of the thioureas and thiosemicarbazides the most studied are the trisubstituted derivatives especially tributyl thiourea. Chemical literature teaches that the most active materials of either class are the trisubstituted derivatives. However, like the lactams, these materials are quite scorchy and thus have found little, if any, commercial use. A substituted olefin is marked by Bayer as a non-discoloring antiozonant but it is only recommended for use in ozone-resistant rubbers such as polychloroprene. In addition to the above-mentioned materials a recent patent claims antiozonant activity for cyanoalkyl esters of dithiocarbamic acids.

This invention discloses a new class of antiozonants which are stable toward dioxygen. Their protective reactivity is specifically directed toward ozone which greatly increases their persistence in rubber. In addition, their molecular weights can be adjusted to improve volatility and water extractability characteristics. An additional benefit of these new antiozonants is that they are largely non-discoloring and non-staining. Thus, they can be used in rubber goods heretofore unable to be protected from the degradative effects of ozone, e.g. white sidewalls on tires, shoe soles, boots and rubbers, and gaskets which come in contact with painted surfaces. Other species in the class have the benefit of being less staining and less discoloring than the para-phenylenediamine derivatives commercially available.

DISCLOSURE OF THE INVENTION

In accordance with the practice of the present invention, there is disclosed a rubber composition comprising a rubber susceptible to ozone degradation and an antiozonant effective amount of a compound selected from the group consisting of compounds represented by the following structural formulae:

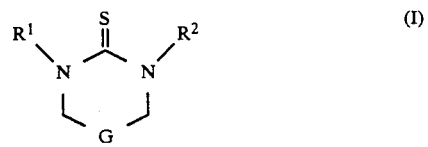

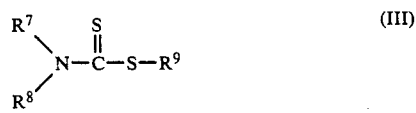

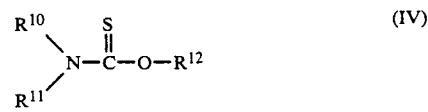

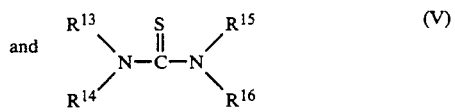

wherein G is selected from the group consisting of →N—R$^3$, —O— and —S—.
wherein R$^1$, R$^2$, R$^3$, R$^4$, R$^5$, R$^7$, R$^8$, R$^{10}$, R$^{11}$, R$^{13}$, R$^{14}$, R$^{15}$ and R$^{16}$ are independently selected from the group consisting of:
(a) alkyl radicals having 1 to 25 carbon atoms,
(b) cycloalkyl radicals having 3 to 25 carbon atoms,
(c) aryl radicals having 6 to 25 carbon atoms; and
(d) radicals selected from the group consisting of those radicals represented by the following structural formulae:

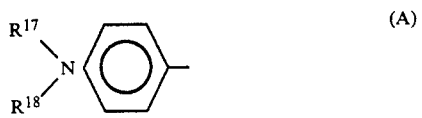

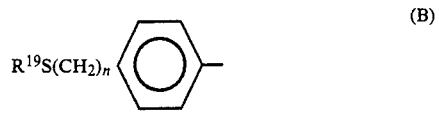

-continued and

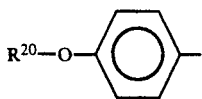
(C)

wherein $R^{17}$, $R^{18}$, $R^{19}$ and $R^{20}$ are independently selected from the group consisting of hydrogen: substituted and unsubstituted alkyl radicals having 1 to 25 carbon atoms: and substituted and unsubstituted aryl radicals having 6 to 25 carbon atoms; n is an integer of 1 to 6:

wherein $R^3$ can also be hydrogen;

wherein $R^6$, $R^9$ and $R^{12}$ are selected from the group of radicals defined by members (a), (b) and (c);

wherein the radicals of members (a), (b) and (c) can be unsubstituted or substituted with the proviso that when a radical from member (a) or (b) is substituted with an amino group, the alpha atom of the radical is free of amino groups, with the proviso that $R^6$ can be a thioamide group so as to form a dithiooxamide and $R^6$ is not an unsubstituted or alkyl substituted 4-hydroxyphenyl radical and further providing that $R^9$ is not a cyanoalkyl group:

wherein, when $R^9$ is substituted with a hetero atom, the hetero atom must be substituted on the $\beta$ or higher carbon atom:

wherein the sum of the carbon atoms of $R^{10}$, $R^{11}$ and $R^{12}$ is 8 to 50;

wherein any of the following pairs of radicals, $R^4$ and $R^5$, $R^4$ and $R^6$, $R^5$ and $R^6$, $R^7$ and $R^8$, $R^7$ and $R^9$, $R^8$ and $R^9$, and $R^{11}$, $R^{10}$ and $R^{12}$, $R^{11}$ and $R^{12}$, $R^{13}$ and $R^{14}$, $R^{13}$ and $R^{15}$ and $R^{14}$ and $R^{15}$ can form a ring structure with the proviso that a ring formed with $R^9$ is not further substituted with a sulfone containing ring.

There is also disclosed a rubber composition comprising a rubber and at least one compound selected from the group consisting of those represented by the following structures:

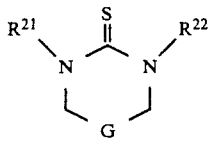
(VI)

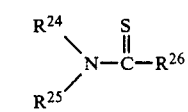
(VII)

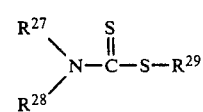
(VIII)

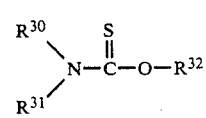
(IX)

and

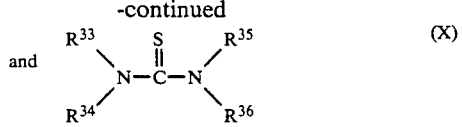
(X)

wherein G is selected from the group consisting of $\rightarrow N-R^{23}$, $-O-$ and $-S-$;

wherein $R^{21}$, $R^{22}$ and $R^{23}$ are independently selected from the group consisting of
(a) alkyl radicals having 1 to 25 carbon atoms,
(b) cycloalkyl radicals having 3 to 25 carbon atoms,
(c) aryl radicals having 6 to 25 carbon atoms, and
(e) radicals selected form the group consisting of those radicals represented by the following structural formulae:

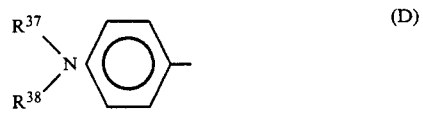
(D)

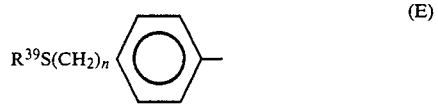
(E)

and
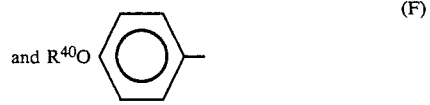
(F)

wherein $R^{37}$, $R^{38}$, $R^{39}$ and $R^{40}$ are independently selected from the group consisting of hydrogen; alkyl radicals having 1 to 25 carbon atoms; and aryl radicals having 6 to 25 carbon atoms; n is an integer of 1 to 6;

wherein the radicals of members (a), (b) and (c) can be unsubstituted or substituted with the proviso that when a radical from members (a) or (b) is substituted with an amino group, the alpha atom of the radical is free of amino groups: $R^{23}$ can also be hydrogen:

wherein when G is $-O-$, at least one of $R^{21}$ and $R^{22}$ must be selected from the radicals in member (e):

wherein $R^{24}$, $R^{25}$ and $R^{26}$ are selected from the group consisting of the radicals designated for $R^{21}$ with the proviso that $R^{26}$ is not an unsubstituted or alkyl substituted 4-hydroxyphenyl radical; $R^{26}$ can be a thioamide group so as to form a dithiooxamide:

wherein $R^{27}$ and are selected from the group consisting of those radicals designated for $R^{21}$ with the proviso that at least one of $R^{27}$ and $R^{28}$ must be selected from the radicals in member (e):

wherein $R^{30}$, $R^{31}$ and $R^{32}$ are selected from the group consisting of those radicals designated for $R^{21}$ with the proviso that the sum of the carbon atoms of $R^{30}$, $R^{31}$ and $R^{32}$ is 8 to 50:

wherein $R^{33}$ $R^{34}$ $R^{35}$ and $R^{36}$ are selected from the group consisting of those radicals designated for $R^{21}$ with the proviso that at least one of $R^{33}$, $R^{34}$, $R^{35}$ and $R^{36}$ be selected from the radicals in member (e);

wherein any of the following pairs of radicals: $R^{24}$ and $R^{25}$, $R^{24}$ and $R^{26}$, and $R^{26}$, $R^{27}$ and $R^{28}$, $R^{27}$ and $R^{29}$, $R^{28}$ and $R^{29}$, $R^{30}$ and $R^{31}$, $R^{30}$ and $R^{32}$, $R^{31}$ and $R^{32}$, $R^{33}$ and $R^{34}$, $R^{33}$ and $R^{35}$, and $R^{34}$ and $R^{35}$ can form a ring structure.

There is also further disclosed a composition of matter selected from the group consisting of compounds represented by the following structural formulae:

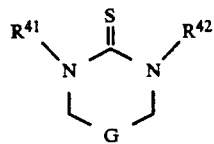
(XI)

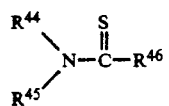
(XII)

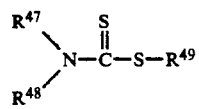
(XIII)

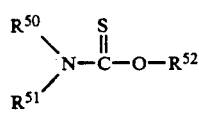
(XIV)

and 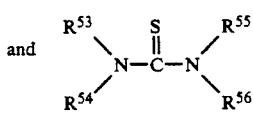
(XV)

wherein G is selected from the group consisting of →N—$R^{43}$,—S— and —O—:

wherein $R^{41}$, $R^{42}$ and $R^{43}$ are independently selected from the group consisting of
(a) alkyl radicals having 1 to 25 carbon atoms,
(b) cycloalkyl radicals having 3 to 25 carbon atoms,
(c) aryl radicals having 6 to 25 carbon atoms, and
(f) radicals selected from the group consisting of those radicals represented by the following structural formulae:

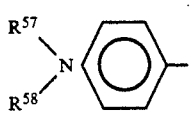
(H)

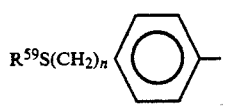
(J)

and 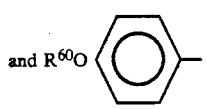
(K)

wherein $R^{57}$, $R^{58}$, $R^{59}$ and $R^{60}$ are independently selected from the group consisting of hydrogen, alkyl radicals having 1 to 25 carbon atoms and aryl radicals having 6 to 25 carbon atoms: n is an integer of 1 to 6:

wherein the radicals of members (a), (b) and (c) can be unsubstituted or substituted with the proviso that when a radical from members (a) or (b) is substituted with an amino group, the alpha atom of the radical is free of amino groups:

wherein, when G is →N—$R^{43}$, at least one of $R^{41}$, $R^{42}$ and $R^{43}$ is selected from the radicals of member (f):

wherein, when G is —O—, at least one of $R^{41}$ and $R^{42}$ is selected from the radicals of member (f):

wherein, when G is —S—, then $R^{41}$ is as defined above and $R^{42}$ must contain at least 3 carbon atoms with the proviso that when $R^{41}$ is phenyl, $R^{42}$ is not phenyl or para-chlorophenyl:

wherein $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$ and $R^{56}$ are independently selected from the group consisting of (a), (b), (c) and (f) above with the proviso that at least one of the radicals attached to a nitrogen atom in structure XII, XIII, XIV or XV is selected from member (f):

wherein $R^{46}$ can be a thioamide group so as to form a dithiooxamide.

Compounds conforming to structural formulae I, VI and XI can be prepared as follows:

Preparation of a 1,3-disubstituted thiourea

Two moles of a primary amine are added to a one-liter, three-neck flask fitted with a mechanical stirrer, addition funnel and a condenser. Next, is added 250 milliliters of a solvent, such as isopropanol. Then 1.1 moles of carbon disulfide are added with stirring, at a rate such that the reflux level is kept to the lower quarter of the condenser. When the addition of the carbon disulfide is complete, the mixture is refluxed with stirring until hydrogen sulfide evolution ceases. The product can be recovered by cooling the mixture and filtering off the product or by distilling out the solvent.

General procedure for preparation of tetrahydro-(S)-triazinethiones

One mole of a 1,3-disubstituted thiourea and two moles of formalin are combined in a two liter flask with 250 mL solvent such as toluene and heated with stirring to 50 to 60° C. More solvent may be needed depending on the thiourea. After 0 to 6 hours, one mole of a primary amine is added and heating is continued overnight. If analysis shows poor conversion of the thiourea, additional formalin and amine are added in a 2 to 1 ratio and the reaction continued. The product may be recovered by appropriate conventional methods such as crystallization and filtration or distillation of the solvent. It may be purified further by such methods as distillation, extraction or chromatography.

Preparation of oxadiazine thiones

The oxadiazine thiones may be prepared similarly to the triazine thiones with the exception that the primary amine is not required. Optionally an acid catalyst may be utilized.

Preparation of thiadiazine thiones

One mole of a 1,3-disubstituted thiourea and two moles of paraformaldehyde are added to a solvent such as chloroform along with an acid catalyst. The mixture is stirred and refluxed while a slow stream of hydrogen sulfide is passed through. After the theoretical amount of water is collected in a reverse phase water separator, the solvent is removed using a rotary evaporator and the residue is recovered.

Preparation of the thioamides of structural formulae II, VII and XII

The thioamides of structural formulae II, VII and XIII can be prepared by reacting sulfur and a secondary amine in the presence of an aldehyde or a ketone by heating and stirring under an inert atmosphere. The product may be recovered by quenching and filtering.

Preparation of the dithiocarbamates of structural formulae III, VIII and XIII

The dithiocarbamates of structural formulae III, VIII and XIII can be prepared by adding a mixture of carbon disulfide and a secondary amine to a solution of sodium hydroxide followed by adding an alkyl halide, refluxing and recovering the product.

Preparation of the thiocarbamate-O-alkyl esters of structural formulae IV, IX and XIV The thiocarbamate-0-alkyl esters of structural formulae IV, IX and XIV can be prepared by mixing a secondary amine in a solvent along with an aqueous carbonate solution followed by the addition of thiophosgene while cooling to remove the heat of reaction. Next is added an alcohol such as methanol, followed by refluxing. The product may be recovered by isolating the organic layer and removing the solvent.

Preparation of the thioureas of structural formulae V, X and XV

Thiophosgene is added to a secondary amine in a solvent such as chloroform while cooling to remove the heat of reaction. Next is added an aqueous carbonate solution followed by refluxing. The product may be recovered by isolating the organic layer and removing the solvent.

The following compounds are representative of the novel composition of matter of the present invention:
tetrahydro-1,3-di-(4-isopropoxyphenyl)-5-butyl-(S)triazine thione;
tetrahydro-1,3-di-(4-isopropoxyphenyl)-5-t-octyl-(S)triazine thione:
tetrahydro-1,3-di-(4-anilinophenyl)-5-t-octyl-(S)triazine thione;
tetrahydro-1,3-di-(4-anilinophenyl)-5-hexadecyl-(S)-triazine thione:
tetrahydro-1,3-di-(4-o-toluidinophenyl)-5-hexadecyl-(S)-triazine thione;
tetrahydro-1,3-bis-(4-diethylaminophenyl)-5-butyl-(S)-triazine thione;
tetrahydro-1,3-bis-(4-diethylaminophenyl)-5-t-octyl-(S)-triazine thione;
tetrahydro-1,3-bis-[4-(1,3-dimethylbutylamino)-phenyl]-5-octyl-(S)-triazine thione:
tetrahydro-1,3-bis-[4-(1,3-dimethylbutylamino)-phenyl]-5-isopropyl-(S)-triazine thione:
tetrahydro-1,3-di-(4-dodecylmercaptomethylphenyl)-5-butyl-(S)-triazine thione:
tetrahydro-1,3-di-(4-dodecylmercaptomethylphenyl)-5-cyclohexyl-(S)-triazine thione:
tetrahydro-1,3-di-(4-isopropylaminophenyl)-5-butyl-(S)-triazine thione:
tetrahydro-1,3-di-(4-isopropylaminophenyl)-5-t-octyl-(S)-triazine thione;
tetrahydro-3,5-di-(4-anilinophenyl)-1,3,5-oxadiazine-4-thione:
tetrahydro-3,5-di-(4-o-toluidinophenyl)-1,3,5-oxadiazine-4-thione;
tetrahydro-3,5-di-(4-isopropylaminophenyl)-1,3,5-oxadiazine-4-thione:
tetrahydro-3,5-bis-(4-diethylaminophenyl)-1,3,5-oxadiazine-4-thione:
tetrahydro-3,5-bis-[4-(1,3-dimethylbutylamino)-phenyl]-1,3,5-oxadiazine-4-thione:
tetrahydro-3,5-di-(4-octylmercaptomethylphenyl)-1,3,5-oxadiazine-4-thione:
tetrahydro-3,5-di-(4-isopropoxyphenyl)-1,3,5-oxadiazine-4-thione:
tetrahydro-3,5-di-(4-isopropoxyphenyl)-1,3,5-thiadiazine-4-thione:
tetrahydro-3-5-di-(4-dodecylmercaptomethylphenyl)-1,3, 5-thiadiazine-4-thione;
tetrahydro-3,5-bis-[4-(1,3-dimethylbutylamino)phenyl]-1,3,5-thiadiazine-4-thione:
tetrahydro-3,5-bis-(4-diethylaminophenyl)-1,3,5-thiadiazine-4-thione:
tetrahydro-3,5-di-(4-o-toluidinophenyl)-1,3,5-thiadiazine-4-thione:
tetrahydro-3,5-di-(4-anilinophenyl)-1,3,5-thiadiazine-4-thione:
tetrahydro-3,5-dibutyl-1,3,5-thiadiazine-4-thione:
tetrahydro-3-phenyl-5-butyl-1,3,5-thiadiazine-4-thione:
tetrahydro-3-cyclohexyl-5-butyl-1,3,5-thiadiazine-4-thione:
N-(4-anilinophenyl)-N-(1,3-dimethylbutyl)-hexanethioamide;
N-(4-anilinophenyl)-N-(1,3-dimethylbutyl)-benzenecarbothioamide:
N-(4-anilinophenyl)-N-isopropylphenylethanethioamide:
N-(4-diethylaminophenyl)-N-methylphenylethanethioamide;
N-(4-diethylaminophenyl)-N-methylcyclohexanecarbothioamide;
N-(4-ethoxyphenyl)-N-methylphenylethanethioamide:
N-(4-dodecylmercaptomethylphenyl)-N-methylphenylethanethioamide:
N-(4-anilinophenyl)-N-methyldithiocarbamate methyl ester:
N-(4-anilinophenyl)-N-isopropyldithiocarbamate methyl ester:
N-[4-(1-methylheptylamino)phenyl]-N-(1-methylheptyl)-dithiocarbamate methyl ester:
N-(4-ethoxyphenyl)-N-methyldithiocarbamate methyl ester:
N-(4-dodecylmercaptomethylphenyl)-N-methyldithiocarbamate methyl ester;
N-(4-diethylaminophenyl)-N-methyldithiocarbamate methyl ester:
N-(4-diethylaminophenyl)-N-methyldithiocarbamate phenyl ester;
N-(4-anilinophenyl)-N-methylthiocarbamate-0-methyl ester:
N-(4-anilinophenyl)-N-isopropylthiocarbamate-0-methyl ester:
N-[4-(1-methylheptylamino)phenyl]-N-(1-methylheptyl)-thiocarbamate-0-methyl ester;
N-(4-ethoxyphenyl)-N-methylthiocarbamate-O-methyl ester;
N-(4-diethylaminophenyl)-N-methyl-thiocarbamate-O-methyl ester;
N-(4-dodecylmercaptomethylphenyl)-N-methyl-thiocarbamate-O-methyl ester:
N-(4-dodecylmercaptomethylphenyl)-N-methyl-thiocarbamate-O-phenyl ester:
1,3-dimethyl-1,3-di-(4-anilinophenyl)-thiourea:
1,3-dimethyl-1,3-bis-(4-diethylaminophenyl)-thiourea:
1,3-dimethyl-1,3-di-(4-isopropylaminophenyl)-thiourea;
1,3-di-(1-methylheptyl)-1,3-di[4-(1-methylheptylamino)phenyl]-thiourea:
1,3-dimethyl-1,3-di-(4-ethoxyphenyl)-thiourea:

1,3-dimethyl-1,3-di-(4-dodecylmercaptomethylphenyl)-thiourea:
N,N'-dimethyl-N,N'-di-(4-dodecylmercaptomethylphenyl)dithiooxamide:
N,N'dimethyl-N,N'-di-(4-methoxyphenyl)-dithiooxamide:
N,N'-di-(1-methylheptyl)-N,N'-di-[4-(1-methylheptylamino)phenyl]-dithiooxamide:
N,N'-dimethyl-N,N'-bis-(4-diethylaminophenyl)-dithiooxamide;
N,N'-dimethyl-N,N'-di-(4-anilinophenyl)-dithiooxamide;

In addition to those compounds immediately above, the following compounds can be used in the rubber compositions of the present invention:
tetrahydro-1,3,5-tributyl-(S)-triazine thione:
tetrahydro-1,3-diethyl-5-cyclohexyl-(S)-triazine thione:
tetrahydro-1,3,5-tricyclohexyl-(S)-triazine thione:
tetrahydro-1,3,5-tribenzyl-(S)-triazine thione:
tetrahydro-1,3-diphenyl-5-butyl-(S)-triazine thione:
tetrahydro-1,3-dibutyl-(S)-triazine thione;
morpholinothiocarbamate-O-butyl ester:
N,N-dibutylthiocarbamate-O-butyl ester:
N,N-dicyclohexylthiocarbamate-O-butyl ester;
N-allylbenzoxazole-2-thione:
N,N-dibutylthiocarbamate-O-phenyl ester;
N,N-(oxydiethylene)-hexanethioamide:
N,N-(oxydiethylene)-benzenecarbothioamide;
N,N-(oxydiethylene)-cyclohexanecarbothioamide:
N,N-(oxydiethylene)-phenylethanethioamide:
N,N-dimethyl-phenylethanethioamide:
N,N-(hexamethylene)-phenylethanethioamide;
N,N,N',N'-tetrabutyldithiooxamide:
bis-pyrrolidinodithiooxamide;
N,N,N',N'-tetracyclohexyldithiooxamide;
tetrahydro-3,5-dibutyl-1,3,5-oxadiazine-4-thione;
tetrahydro-3,5-dicyclohexyl-1,3,5-oxadiazine-4-thione;
tetrahydro-3,5-diphenyl-1,3,5-oxadiazine-4-thione;
tetrahydro-3,5-dibenzyl-1,3,5-oxadiazine-4-thione:
tetrahydro-3-phenyl-5-butyl-1,3,5-oxadiazine-4-thione;
morpholinodithiocarbamate butyl ester:
N,N-dicyclohexyldithiocarbamate methyl ester:
N,N-dibutyldithiocarbamate cyclohexyl ester:
N-methylbenzothiazole-2-thione: and
N,N-dibutyldithiocarbamate phenyl ester.

Preferred compounds are the following:
tetrahydro-1,3-di-(4-isopropoxyphenyl)-5-butyl-(S)-triazine thione;
tetrahydro-1,3-di-(4-isopropoxyphenyl)-5-t-octyl-(S)-triazine thione:
tetrahydro-1,3-di-(4-anilinophenyl)-5-t-octyl-(S)triazine thione:
tetrahydro-1,3-bis-(4-diethylaminophenyl)-5-butyl-(S)-triazine thione:
tetrahydro-1,3-bis-(4-diethylaminophenyl)-5-t-octyl-(S)-triazine thione:
tetrahydro-1,3-bis-[4-(1,3-dimethylbutylamino)phenyl]-5-octyl-(S)-triazine thione:
tetrahydro-1,3-bis-[4-(1,3-dimethylbutylamino)phenyl]-5-isopropyl-(S)-triazine thione:
tetrahydro-1,3-di-(4-isopropylaminophenyl)-5-butyl-(S)-triazine thione;
tetrahydro-1,3-di-(4-isopropylaminophenyl)-5-t-octyl-(S)-triazine thione:
tetrahydro-3,5-di-(4-isopropylaminophenyl)-1,3,5-oxadiazine-4-thione:
tetrahydro-3,5-bis-(4-diethylaminophenyl)-1,3,5-oxadiazine-4-thione:
tetrahydro-3,5-bis-[4-(1,3-dimethylbutylamino)phenyl]-1,3,5-oxadiazine-4-thione;
tetrahydro-3,5-di-(4-octylmercaptomethylphenyl)-1,3,5-oxadiazine-4-thione;
tetrahydro-3,5-di-(4-isopropoxyphenyl)-1,3,5-oxadiazine-4-thione;
N-(4-anilinophenyl)-N-isopropylphenylethanethioamide:
N-(4-diethylaminophenyl)-N-methylphenylethanethioamide:
N-(4-ethoxyphenyl)-N-methylphenylethanethioamide:
N-(4-dodecylmercaptomethylphenyl)-N-methylphenylethanethioamide:
N-(4-anilinophenyl)-N-methyldithiocarbamate methyl ester:
N-(4-anilinophenyl)-N-isopropyldithiocarbamate methyl ester:
N-(4-ethoxyphenyl)-N-methyldithiocarbamate methyl ester;
N-(4-dodecylmercaptomethylphenyl)-N-methyldithiocarbamate methyl ester:
N-(4-diethylaminophenyl)-N-methyldithiocarbamate methyl ester:
N-(4-anilinophenyl)-N-methylthiocarbamate-O-methyl ester:
N-(4-anilinophenyl)-N-isopropylthiocarbamate-O-methyl ester:
N-(4-ethoxyphenyl)-N-methylthiocarbamate-O-methyl ester:
N-(4-diethylaminophenyl)-N-methylthiocarbamate-O-methyl ester:
N-{4-dodecylmercaptomethylphenyl)-N-methyl-thiocarbamate-O-methyl ester;
1,3-dimethyl-1,3-bis-(4-diethylaminophenyl)-thiourea;
1,3-dimethyl-1,3-di-(4-isopropylaminophenyl)-thiourea;
1,3-dimethyl-1,3-di-(4-ethoxyphenyl)-thiourea;
1,3-dimethyl-1,3-di-(4-dodecylmercaptomethylphenyl)-thiourea;
tetrahydro-1,3,5-tributyl-(S)-triazine thione;
tetrahydro-1,3-diethyl-5-cyclohexyl-(S)-triazine thione;
N,N-(oxydiethylene)-phenylethanethioamide;
tetrahydro-3,5-dibutyl-1,3,5-oxadiazine-4-thione;
tetrahydro-3,5-dicyclohexyl-1,3,5-oxadiazine-4-thione;
morpholinothiocarbamate-0-butyl ester;
morpholinodithiocarbamate butyl ester;

EXAMPLE 1

Preparation of tetrahydro-5-(t)-butyl-1,3-di-n-butyl-(S)-triazinethione

Formalin (40.5g; 37%; 0.50 mol) and 1,3-dibutyl thiourea (47.1 g: 0.25 mol) were combined in a 500 mL Erlenmeyer flask and heated to approximately 50° C. Sufficient isopropanol was added to yield a homogeneous solution which was heated for 6 hours after which t-butyl amine (18.31 g: 0.25 mol) was added. Additional isopropanol was required to maintain homogeneity. After stirring at reflux overnight, the isopropanol was stripped off on a rotary evaporator. The residue was diluted with 200 mL of 75/25, v/v, ether/hexane solution, washed with dilute acetic acid, water and saturated $NaHCO_3$. After drying with $K_2CO_3$, the solvent was removed on a rotary evaporator to give 67.2 g (94% yield) light yellow oil which was approximately 85% pure as analyzed by NMR.

The major impurity appeared to be dibutyl thiourea.

EXAMPLE 2

Preparation of tetrahydro-5-cyclohexyl-1,3-di-n-butyl-(S)-triazinethione

Formalin (40.5 g: 37%: 0.50 mol) and 1,3-dibutyl thiourea (47.1 g: 0.25 mol) were heated together in a 250 mL Erlenmeyer flask at 50–60° C. for 1 hour. Cyclohexyl amine (24.8 g: 0.25 mol) was added and heating continued overnight. Analysis of the crude product by NMR showed 50 % reaction so an additional 30 g (0.21 mol) formalin and 18.2 g (0.18 mol) cyclohexyl amine was added and heating continued for an additional 6 hours. The reaction product was recovered by separating the aqueous layer, extracting it with two 100 mL portions of 75/25, v/v, ether/hexane solution and washing the combined organic layers with dilute acetic acid, water and saturated $NaHCO_3$. After drying the organic solution with $K_2CO_3$, the solvent was removed on the rotary evaporator. NMR analysis indicated a conversion of 75%. This mixture was combined with 10 g (0.12 mol) formalin and sufficient isopropanol to yield a homogeneous solution and allowed to sit at room temperature over the weekend. Cyclohexyl amine (7 g: 0.07 mol) was added and the mixture refluxed for 7 hours, then the reaction product was recovered as above to yield 75.1 g (97% yield) amber oil approximately 95% pure analyzed by NMR.

EXAMPLE 3

Preparation of tetrahydro-5-cyclohexyl-1,3-diethyl-(S)-triazinethione

Formalin (1344 g: 37%: 16.4 mol), 1,3-diethyl thiourea (983 g: 7.4 mol) and NaOH (3 g: 0.075 mol) were combined in a 5L-3-neck flask with 1L isopropanol and allowed to stand overnight. Cyclohexylamine (894g; 9.0 mol) was added with stirring over 3 hours. The reaction was then heated to reflux overnight. An additional 400 g (4.9 mol) formalin was added, the mixture heated for 8 hours and 250g (2.5 mol) cyclohexyl amine added. After refluxing overnight, the aqueous layer was drawn off and the isopropanol distilled to a pot temperature of 110° C. The residue was diluted 1:1 v/v, with 50/50, v/v, toluene/hexane solution, extracted with 10% HCl till the wash was acidic, then with water and saturated $NaHCO_3$ solution After drying with $K_2CO_3$ the solution was cooled to collect the product. Additional material was collected by concentration of the mother liquors to give 940 g (50% yield) of a white solid, mp. 73–75° C. An additional 410 g was recovered from the mother liquors after stripping on a rotary evaporator by continuous extraction with hexane.

EXAMPLE 4

Preparation of tetrahydro-3,5-dibutyl-1,3,5-oxadiazine-4-thione

Formalin (18 g: 37%: 0.22 mol) and 1,3-dibutyl thiourea (18.8g; 0.10 mol) were combined in a 1-neck 250 mL round bottom flask with 50 mL isopropyl alcohol. Concentrated HCl (1g) was added and the mixture was refluxed for 8 hours. An additional 1g of concentrated HCl was then added and reflux continued overnight. The solvent was removed on a rotary evaporator, the product taken up in dichloromethane and washed with saturated $NaHCO_3$ solution The organic layer was dried with $MgSO_4$ and the solvent removed on a rotary evaporator to yield 22g (96%) of a yellow oil.

Other oxadiazine thiones are similarly prepared from the appropriate thiourea as above or as described Seidel and Boettner, *J Heterocyclic Chemistry:* 9(2): 231–4 (1972).

EXAMPLE 5

Preparation of 1,3-di-(4-anilinophenyl)-thiourea

Para-aminodiphenylamine (1917g:10.4 mol) was weighed into a 12 L, 3-neck flask and 5 L isopropanol added. Carbon disulfide (476g: 6.25 mol) was added with stirring over the course of 2 hours. The mixture was then heated to reflux for 7 hours, the evolved $H_2S$ being trapped in a NaOH solution. After cooling, the product was filtered off, washed with isopropanol and air dried. Yield 1872g (88%) of a grey solid, mp 164–71° C.

EXAMPLE 6

Preparation of tetrahydro-1,3-di-(4-anilinophenyl)-5-butyl-(S)-triazine thione

The 1,3-di-(4-anilinophenyl)-thiourea, from Example 5, (41g: 0.10 mol) was dissolved in 100 mL THF and formalin (16.8g: 0.21 mol) added. This mixture was refluxed 0.5 hours after which butyl amine (7.7g: 0.105mol) made up to 25 mL in THF was added in one portion. Heating was continued for 22 hours after which the reaction was cooled and the crystalline product collected, to yield 29.8g (59%) of white crystals, mp 202.5–204° C.

EXAMPLE 7

Preparation of tetrahydro-1,3-di-(4-anilinophenyl)-5-(t)-octyl-(S)-triazine thione The 1,3-di-(4-anilinophenyl)-thiourea, from Example 5, (205g: 0.50 mol), formalin (86g, 37%: 1.05 mol) and t-octyl amine (68g: 0.52 mol) were combined in a 1L-1-neck flask with 300 mL acetonitrile. The mixture was heated at reflux for 10 hours, then the solvent stripped on a rotary evaporator. On mixing the residual oil with toluene, a white solid immediately formed which was filtered off and dried, to yield 253g (90%); mp 154–156° C. The corresponding 5-tallowamine, mp 65–120° C., 5-cocoamine, mp 151–154C° and 5-Jeffamine ™ M-360 derivatives were prepared in a similar fashion.

EXAMPLE 8

Preparation of N,N,N',N'-tetrabutyloxamide

Sodium metal (0.5g, 0.02 mol) was reacted with a mixture of dibutylamine (65g, 0.50 mol) and 2mL isopropanol. When the sodium had disappeared, diethyl oxalate (29.2g, 0.20 mol) was added and the mixture refluxed overnight. The reflux condenser was then replaced with a distillation head and the ethanol formed in the reaction and excess dibutyl amine distilled off. The residue was diluted with methylene chloride, washed with dilute HCl, water and 5% $NaHCO_3$ solution and dried with $MgSO_4$. The solvent was stripped off and the product flash distilled in vacuo, to yield 49.7g (80%).

EXAMPLE 9

Preparation of N,N,N',N'-Tetrabutyldithiooxamide

The tetrabutyloxamide from above (49.7g, 0.16 mol) was dissolved in 50mL pyridine. $P_2S_5$ (18.5g, 0.083 mol) was added in one portion and rinsed in with an additional 50 mL pyridine. The mixture was refluxed with stirring for 4 hours after which the reflux condenser was replaced with a distillation head and the pyridine distilled off. The residue was poured over ice and allowed to stand overnight to hydrolyze any unreacted $P_2S_5$. The mixture was then extracted with 3-150 mL portions of methylene chloride. The combined organic extracts were washed with 50 mL water and 100 mL of 5% $NaHCO_3$ solution then dried with $MgSO_4$. The solvent was stripped off and the crude material flash distilled under vacuum, after which the product crystallized. Recrystallization from methanol by cooling in a refrigerator gave 39g product; mp 35-38° C.

EXAMPLE 10

Preparation of dipyrrolidinooxamide

Pyrrolidine (30g, 0.42 mol) was added in one portion to diethyl oxalate (14g, 0.10 mol) in a 100 mL round bottom flask resulting in an immediate, very exothermic reaction. When the heat of reaction had dissipated somewhat, sulfuric acid (0.2g, 0.002 mol) was added and the stirred mixture was refluxed overnight through a 12" fractionating column packed with glass beads. The ethanol formed in the reaction and excess pyrrolidine were then fractionally distilled off and the product poured into a porcelain dish where it immediately crystallized. It was then transferred to a separatory funnel, in methylene chloride solution, where it was washed successively with 50 mL saturated NaCl solution, 25 mL dilute HCl and 50 mL of 5% $NaHCO_3$, solution The solution was then dried with $MgS0_4$ and the solvent stripped off to yield 17g (87%) of the desired product: mp 84-86.520 C.

EXAMPLE 11

Preparation of bis-pyrrolidinodithiooxamide

This was made following the procedure for the tetrabutyl derivative in Example 9 with the following modifications. The reaction of dipyrrolidinooxamide and $P_2S_5$ was exothermic so reaction time was cut to 2 hours. Removal of the solvent after workup gave a light yellow solid (mp 191-94° C.) which showed no major impurities when analyzed by IR or NMR and therefore was not recrystallized.

EXAMPLE 12

Preparation of Tetrahydro-3,5-diethyl-1,3,5-thiadiazine-4-thione

This is prepared as described by Seidel and Boettner: a solution of 26.4g (0.2 mol) of 1,3-diethylthiourea, 12g (0.4 mol) of paraformaldehyde and 5g of p-toluenesulfonic acid in 200 mL of chloroform is refluxed while a slow stream of hydrogen sulfide is passed through. After 1 ½ hours the theoretical amount of water is collected in a reversed phase water separator. The solvent is then removed using a rotary evaporator and the residue recrystallized twice from methylcyclohexane, yield 23g: mp 94-97° C.

Other thiadiazine thiones can be prepared similarly from the corresponding thiourea.

EXAMPLE 13

Preparation of 1,3-dimethyl-1,3-bis-(4-diethylamino-phenyl)-thiourea

N-N-diethyl-N'-methyl-p-phenylenediamine (35.6g, 0.2 mol) is placed in a 250 mL, 3-neck flask with 100

Thiophosgene (11.5g, 0:10 mol) in 20mL chloroform is added with stirring at a rate sufficient to maintain reflux. The mixture is stirred until it returns to room temperature at which point 30g (0.22 mol) of $K_2CO_3$ is added as a saturated aqueous solution. The mixture is then refluxed with stirring overnight. After cooling, the layers are separated, the aqueous layer is extracted once with 50mL chloroform and the combined organic layers are dried with $MgSO_4$. The product is recovered by stripping the solvent on the rotary evaporator.

EXAMPLE 14

Preparation of N-(4-anilinophenyl)-N-(1,3-dimethyl-butyl)-dithiocarbamate methyl ester N-phenyl-N'-(1,3-dimethylbutyl)-p-phenylenediamine (26.8g, 0.10 mol) is dissolved in 100 mL tetrahydrofuran in a 250 mL, 3-neck round bottom flask. Carbon disulfide (7.6g, 0.10 mol) is added over 0.5 hours with the concurrent addition of an aqueous solution of sodium hydroxide (4.0g, 0.10 mol). When addition is complete, methyl iodide (14.2g, 0.10 mol) is added and the mixture refluxed for 1 hour. The solvent is then stripped off on a rotary evaporator and the residue extracted with methylene chloride. The extract is dried with $MgSO_4$ and the solvent is again removed on the rotary evaporator to yield the product.

EXAMPLE 15

Preparation of N-(4-anilinophenyl)-N-(1,3-dimethyl-butyl)-thiocarbamate-O-methyl ester N-phenyl-N'-(1,3-dimethylbutyl)-p-phenylenediamine (26.8g, 0.10 mol) in 100 mL chloroform and 30g (0.22 mol) of $K_2CO_3$ as a saturated aqueous solution are placed in a 250 mL, 3-neck round bottom flask. Thiophosgene (11.5g: 0.10 mol) in 20 mL chloroform is added at such a rate sufficient to reach and maintain reflux conditions. Stirring is continued until the mixture returns to room temperature. Methanol (6.4g, 0.2 mol) is then added and the mixture refluxed for 4 hours. The organic layer is separated, dried with $MgSO_4$ and the solvent removed on a rotary evaporator to give the desired product.

The following thioamides were prepared according to the following procedure:

0.50 moles of sulfur, 0.52 moles of morpholine and 0.50 moles of either a base aldehyde or a base ketone were mixed in a nitrogen-flushed 250 mL 2-neck round bottom flask equipped with stirring bar, thermometer and a reflux condenser topped by a nitrogen inlet. The mixture was heated to a pot temperature of 100° C. and stirred 18-20h under a slight positive pressure of nitrogen. The product was then poured onto ice and extracted into dichloromethane. The solution was dried with sodium sulfate, filtered and concentrated on a rotary evaporator.

EXAMPLE 16

Preparation of
N,N-(oxydiethylene)-benzenecarbothioamide

Using a base of benzaldehyde, the product recrystallized from methanol was a light yellow crystalline solid, yield 80%, mp 135–137° C.

EXAMPLE 17

Preparation of N,N-(oxydiethylene)-phenylethane thioamide

Using acetophenone as the base, the product recrystallized from methanol was a white crystalline solid, yield 70%, mp 78.5–80° C.

EXAMPLE 18

Preparation of N,N-(oxydiethylene)-phenylpropane thioamide

Using propiophenone as the base, the product was distilled as an orange liquid, yield 92%, bp 155–162° C. @ 0.3 mm Hg.

EXAMPLE 19

Preparation of N,N-(oxydiethylene)-4-methylpentane thioamide

Using methylisobutylketone as the base, the product was distilled as a light orange liquid, yield 76%, bp 105–115° C. @ 0.2 mm Hg.

EXAMPLE 20

Preparation of N,N-(oxydiethylene)-hexanethioamide

Using hexanal as the base, the product was distilled as a light orange liquid, yield 89%, bp 115–125° C. @ 0.2 mm Hg.

The rubbers which can be used in the compositions of this invention are those in the general class of non-halogenated diene polymers. Included in, but not limited to, those polymers are the following: natural rubber, also known as polyisoprene, and synthetic polymers which are polymers prepared from a single monomer (homopolymer) or a mixture of two or more copolymerizable monomers (copolymers) wherein the monomers are combined in a random distribution or block form. Representative of the synthetic polymers are polybutadiene, polyisoprene, polyethylbutadiene, polydimethylbutadiene, polypentadiene, polydicyclopentadiene, polyhexadiene, polypiperylene, polyacrylonitrile, copolymers of diene monomers with olefin, cycloolefin or vinyl monomers such as styrene-butadiene copolymers, styrene-isoprene copolymers, acrylonitrile-butadiene copolymers, ethylene-propylene-diene copolymers, isobutene-isoprene copolymers and the like.

When the compounds of the present invention are used in the rubber compositions of this invention either singly or in combinations, the total level to be effective as antiozonants is from about 2.5 to 10 parts by weight, preferably 3.0 to 7.0 parts by weight based on 100 parts by weight of the rubber polymer (hereinafter, phr). Greater or lesser amounts can be used, however, depending upon the severity of the conditions to which the rubber composition will be submitted. When the compounds of the present invention are used in rubber compositions to enhance known antiozonants, they can be used at a level of at least 0.1 phr, preferably at least 0.5 phr.

It should be readily apparent to those skilled in the art of rubber compounding that some of the compounds used in some of the embodiments of this invention have been used in rubber compositions as vulcanization accelerators, particularly for halogenated dienes such as polychloroprene. It is believed that analogs of the compounds of the present invention having a hydrogen attached to the nitrogen adjacent to the thiocarbonyl group would also function as accelerators and thus destroy functionality as an antiozonant. Furthermore it is believed that the presence of some substituents e.g. a nitrogen atom on a carbon atom alpha to the thiocarbonyl group would decompose at vulcanization temperatures to form a vulcanization accelerator.

The following examples are intended to illustrate, not to limit, the practice of the present invention.

EXAMPLE 21

Preparation of N-isopropyl-p-phenylenediamine

A 500 mL, 3-neck flask was charged with 86g(0.57mol) of p-aminoacetanilide, 50g(0.64 mol) of isopropyl chloride and 100mL of N-methylpyrrolidinone and heated to reflux for 24 hours. The mixture was then poured into 700 mL of water, neutralized with NaOH and extracted with 4-100 mL portions of ether. The combined ether fractions were backwashed with 100 mL of water and the ether removed on a rotary evaporator. The product, contaminated with residual N-methylpyrrolidinone, was hydrolyzed by heating in concentrated HCl for 1 hour. After cooling, it was neutralized with NaOH solution, diluted with water and extracted with 4-100 mL portions of ether. The combined extracts were backwashed with 2–50 mL aliquots of water, dried over $K_2CO_3$ and the ether removed on the rotary evaporator to yield 31g of material. Analysis by NMR indicated it was a mixture of the desired material with 50% N-methylpyrrolidinone.

EXAMPLE 22

Preparation of
1,3-di-(4-isopropylaminophenyl)-thiourea

The crude N-isopropyl-p-phenylenediamine from above was combined with 4.3g(0.056 mol) carbon disulfide in a 100 mL flask. The mixture was slowly brought to approximately 115° C. and then held there until evolution of $H_2S$ ceased. The resulting solution was poured into water to yield a light yellow solid melting at body temperature. On air drying it turned dark brown. Yield 20g, (114%).

EXAMPLE 23

Preparation of
N-(1,3-dimethylbutyl)-p-phenylenediamine

In a 1L, 3-neck flask were combined p-aminoacetanilide (100g:0.67 mol), methyl isobutyl ketone (350g:3.5 mol) and Amberlyst ® 15 resin (5g). The flask was heated with stirring overnight, collecting 11mL water (92% of theory) in a Dean-Stark trap. The catalyst resin was filtered off and the excess ketone removed on a rotary evaporator to yield 154 g of the intermediate Schiff base. This material was dissolved in 200 mL methanol and transferred to a 600 mL beaker. To it was added a solution of 25g (0.66 mol) of $NaBH_4$ in 100 mL of 0.5 M aqueous NaOH in small portions. When the addition was complete, the mixture was heated at 50° C. for 2 hours. The solution was then cooled, carefully made strongly acidic with 15% HCl and refluxed for 2 hours. After cooling, the solution was made basic with careful addition of solid Na₂CO₃ and extracted with ether. The organic solution was dried with K₂CO₃ and the ether removed on the rotary evaporator to yield 128g (99%) of the desired amine.

EXAMPLE 24

Preparation of tetrahydro-1,3-bis-[4-(1,3-dimethyl-butylamino)-phenyl]-5-octyl-(S)-triazinethione A 1L, 3-neck flask was charged with 250g (1.30 mol) of N-(1,3-dimethylbutyl)-p-phenylenediamine and 300 mL of acetonitrile. While stirring, carbon disulfide (53g: 0.70 mol) was added dropwise. When addition was complete, the mixture was heated until H₂S evolution was complete. It was then cooled and formalin (120g: 1.5 mol) and n-octyl amine (86g: 0.66 mol) were added. The mixture was refluxed overnight. The solvent was removed on a rotary evaporator and the residual, syrupy material taken up in methanol. Prolonged cooling in the freezer yielded 112g (30%) of the product, mp 143-6° C.

EXAMPLE 25

Tetrahydro-1,3,5-tributyl-(S)-triazine thione (1,3,5 TBTT) and tetrahydro-5-cyclohexyl-1,3-diethyl-(S)-triazine thione (5-Ch-1,3DETT) were each added at 4.0 parts and 6.0 parts per 100 parts, all by weight, (hereinafter, phr) to a 50/50 blend of a natural rubber (NR) and a polybutadiene (PBD) according to the formulation as shown in Table I to prepare a rubber composition according to the present invention for comparison versus a control composition containing no antiozonant (AOZ).

TABLE I

| Material | phr |
|---|---|
| NR-SMR#5 | 50.00 |
| PBD-BUDENE ™ 1207* | 50.00 |
| Carbon Black | 55.00 |
| Oil | 10.00 |
| Fillers | 7.00 |
| Antioxidant - Wingstay ™ 29* | 2.00 |
| Curatives | 3.15 |
| Antiozonant | as specified |

*Trademark of The Goodyear Tire & Rubber Company

The stocks were cured at 150° C. for the times shown in Table II. Stress/strain properties were tested according to ASTM method D-412 on the original samples and on samples which had been exposed to 50 parts per hundred million (pphm), ozone at 40° C. for 8h and 24 h. Percent tensile retention and percent 100% Modulus retention on the exposed samples were used as a measure of antiozonant effectiveness as shown in Table II.

TABLE II

| Sample | phr | Cure Time, Min | % Tensile Retention 8 h | % Tensile Retention 24 h | % 100% Modulus Retention 8 h | % 100% Modulus Retention 24 h |
|---|---|---|---|---|---|---|
| No AOZ | — | 12 | 55 | 43 | 83 | 72 |
| 1,3,5TBTT | 4 | 5 | 60 | 64 | 93 | 82 |
| 1,3,5TBTT | 6 | 5 | 61 | 65 | 95 | 99 |
| 5-Ch-1,3DETT | 4 | 7.5 | 60 | 56 | 95 | 81 |
| 5-Ch-1,3DETT | 6 | 7.5 | 77 | 76 | 106 | 95 |

EXAMPLE 26

The same two materials form Example 25 were each added at 3.0 phr and 5.0 phr to a styrene-butadiene copolymer (SBR) composition as shown in Table III.

TABLE III

| Material | phr |
|---|---|
| SBR 1502 | 100.00 |
| Carbon Black | 50.00 |
| Fillers | 7.00 |
| Oil | 5.00 |
| Antioxidant - Wingstay ™ 29 | 1.00 |
| Curatives | 3.00 |
| Antiozonant | as specified |

The stocks were cured at 150° C. for the times shown in Table IV. Stress/strain properties were run identically to Example 25. Results are shown in Table IV.

TABLE IV

| Sample | phr | Cure Time, Min | % Tensile Retention 8 h | % Tensile Retention 24 h | % 100% Modulus Retention 8 h | % 100% Modulus Retention 24 h |
|---|---|---|---|---|---|---|
| No AOZ | — | 20 | 54 | 78 | 96 | 90 |
| 1,3,5TBTT | 3 | 20 | 98 | 72 | 104 | 102 |
| 1,3,5TBTT | 5 | 15 | 89 | 92 | 137 | 100 |
| 5-Ch-1,3DETT | 3 | 17 | 102 | 75 | 97 | 86 |
| 5-Ch-1,3DETT | 5 | 15 | 86 | 73 | 106 | 113 |

EXAMPLE 27

Tetrahydro-1,3-bis-[4-(1,3-dimethylbutylamino)-phenyl]-5-octyl-(S)-triazine thione (1,3DBA50TT) and tetrahydro-1,3-di-(4-anilinophenyl)-5-t-octyl-(S)-triazine thione (DAP50TT) were each added at a level of 3.0 phr to a synthetic polyisoprene (IR) according to the formulation shown in Table V, to prepare a rubber composition of the present invention along with a control stock containing no antiozonant.

TABLE V

| Material | phr |
|---|---|
| IR, NATSYN ™ 2200* | 100.00 |
| HAF Carbon Black | 35.00 |
| Oil | 5.00 |
| Fillers | 5.00 |
| Curatives | 3.45 |
| Antiozonant | as specified |

*Trademark of The Goodyear Tire & Rubber Company

Sheets (2 mm thick) from each stock were cured @ 150° C. for the times shown in Table VI after which specimens were prepared and used to run the ICI Annulus Ozone Test as described in a Technical Information Bulletin issued 1.3.71 by Application Research and Technical Service Department, Dyestuffs Division, Imperial Chemical Industries Limited, based upon a paper by Amsden, C.S., Transactions of the Institution of the Rubber Industry, Vol. 13, No. 3, June 1966. The results shown in Table VI are the threshold elongations below which cracking did not occur on specimens exposed to 50 pphm ozone at 40° C. for the time periods listed in Table VI.

TABLE VI

| Sample | Cure Time, Min | Threshold Elongation, % at Exposure Time 2 h | 4 h | 6 h |
|---|---|---|---|---|
| No AOZ | 12 | 20 | 0 | 0 |

TABLE VI-continued

| Sample | Cure Time, Min | Threshold Elongation, % at Exposure Time | | |
|---|---|---|---|---|
| | | 2 h | 4 h | 6 h |
| 1,3DBA5OTT | 9 | 30 | 30 | 30 |
| DAP5OTT | 10 | 25 | 25 | 25 |

EXAMPLE 28

Tetrahydro-1,3,5-tributyl-(S)-triazine thione (1,3,5TBTT) and commercially available N-(1,3-dimethylbutyl)-N'-phenyl-p-phenylene diamine (WS300) were each used alone and in various combinations with each other in an SBR formulation as shown in Table VII. specimens were prepared for the ICI Annulus Ozone Test as described in Example 27. The various levels used and the threshold elongations after 8 hr exposure to 50 pphm ozone are listed in Table VIII.

TABLE VII

| Material | phr |
|---|---|
| SBR 1502 | 100.00 |
| Fillers | 72.00 |
| Oil | 5.00 |
| Curatives | 3.25 |
| Antiozonant | as specified |

TABLE VIII

| | WS300,phr | | |
|---|---|---|---|
| | 0 | 1 | 2 |
| 1,3,5TBTT,phr | Threshold Elongation, % | | |
| 0 | 10 | 30 | 35 |
| 2 | 13 | 25 | 100 |
| 4 | 17 | 100 | 100 |

The results are an indication of the synergy which occurs between a compound of the present invention and a commercially available para-phenylenediamine antiozonant.

EXAMPLE 29

N,N-(oxydiethylene)-phenylethanethioamide (N,N-ODPET) and N,N-(oxydiethylene)-hexanethioamide (N,N-ODHT) were added at the level specified to a styrene-butadiene copolymer (SBR) composition as shown in Table IX.

TABLE IX

| Material | phr |
|---|---|
| SBR 1502 | 100.00 |
| Fillers | 72.00 |
| Oil | 5.00 |
| Curatives | 3.25 |
| Antiozonant | as specified | the stocks were cured at 150° C. for the times shown in Table X. Stress/strain properties were run identically to Example 25. Results are shown in Table X.

TABLE X

| Sample | phr | Cure Time Min | % Tensile Retention | | % 100% Modulus Retention | |
|---|---|---|---|---|---|---|
| | | | 8 h | 24 h | 8 h | 24 h |
| No AOz | — | 20 | 71 | 45 | 94 | 68 |
| N,N-ODPET | 2.48 | 22 | 103 | 94 | 85 | 87 |
| N,N-ODHT | 2.25 | 17 | 74 | 56 | 102 | 83 |

EXAMPLE 30

Tetrahydro-1,3,5-(S)-triazine thione (1,3,5-TBTT), tetrahydro-5-cyclohexyl-1,3-diethyl-(S)-triazine thione (5-Ch-1,3-DETT), N-N-(oxydiethylene)-phenylethane thioamide (N,N-ODPET) and N,N-(oxydiethylene)-4-methylpentanethioamide (N,N-ODMPT) were added at the level specified to an acrylonitrile-butadiene copolymer (NBR) composition as shown in Table XI.

TABLE XI

| Material | phr |
|---|---|
| Chemigum N-615B | 100.00 |
| FEF Black | 50.00 |
| Curatives | 6.90 |
| Antiozonant | as specified |

The stocks were cured at 150° C. for the times shown in Table XII. Results are shown in Table XII.

TABLE XII

| Sample | phr | Cure Time Min | % Tensile Retention | | % 100% Modulus Retention | |
|---|---|---|---|---|---|---|
| | | | 8 h | 24 h | 8 h | 24 h |
| No AOz | — | 20 | 69 | 57 | 92 | 84 |
| 1,3,5-TBTT | 5.32 | 23 | 90 | 78 | 112 | 82 |
| 5-Ch-1,3-DETT | 5.00 | 26 | 83 | 73 | 96 | 91 |
| N,N-ODPET | 4.13 | 16 | 88 | 83 | 103 | 94 |
| N,N-ODMPT | 3.75 | 22 | 82 | 81 | 102 | 92 |

EXAMPLE 31

N-methylbenzothiazole-2-thione (MBTT), 3-methyl-2-thiazolidinethione (MTT), and tetrahydro-3,5-dimethyl-1,3,5-oxadiazinethione (3,5-DMODT) were added at the level specified to a styrene-butadiene copolymer (SBR) composition as shown in Table XIII.

TABLE XIII

| Material | phr |
|---|---|
| SBR 1502 | 100.00 |
| Fillers | 72.00 |
| Oil | 5.00 |
| Curatives | 3.25 |
| Antiozonant | as specified |

The stocks were cured at 150° C. for the times shown in Table XIV. Stress/strain properties were run identically to Example 25. Results are shown in Table XIV.

TABLE XIV

| Sample | phr | Cure Time Min | % Tensile Retention | | % 100% Modulus Retention | |
|---|---|---|---|---|---|---|
| | | | 8 h | 24 h | 8 h | 24 h |
| No AOz | — | 32 | 97 | 64 | 81 | 71 |
| MBTT | 2.1 | 30 | 81 | 56 | 104 | 96 |
| MTT | 1.6 | 29 | 104 | 104 | 98 | 113 |
| 3,5-DMODT | 1.7 | 29 | 92 | 100 | 92 | 88 |

EXAMPLE 32

Tetrahydro-1,3-di-(4-toluidinophenyl)-5-butyl-(S)-triazinethione (1,3DTP5BTT), tetrahydro-1,3-bis-(4-dimethylaminophenyl)-5-butyl-(S)-triazinethione (1,3DMA5BTT), tetrahydro-1,3-bis-(4-(1,3-dimethylamino)-phenyl)-5-octyl-(S)-triazinethione (1,3DBA5OTT), tetrahydro-1,3-di-(4-anilinophenyl)-5-tert-octyl-(S)-triazinethione (1,3DAP5TOTT), and tetrahydro-1,3-bis-(4-diethylaminophenyl)-5-hexadecyl-(S)-triazinethione (1,3DEA5HTT) were added at the level specified to a styrene-butadiene copolymer (SBR) composition as shown in Table XV.

TABLE XV

| Material | phr |
| --- | --- |
| SBR 1502 | 100.00 |
| Fillers | 72.00 |
| Oil | 5.00 |
| Curatives | 3.25 |
| Antiozonant | as specified |

The stocks were cured at 150° C. for the times shown in Table XVI. Stress/strain properties were run identically to Example 25. Results are shown in Table XVI.

TABLE XVI

| Sample | phr | Cure Time Min | % Tensile Retention 8 h | % Tensile Retention 24 h | % 100% Modulus Retention 8 h | % 100% Modulus Retention 24 h |
| --- | --- | --- | --- | --- | --- | --- |
| No AOz | — | 38 | 44 | 36 | 80 | 68 |
| 1,3DTP5BTT | 6.0 | 24 | 85 | 61 | 91 | 64 |
| 1,3DMA5BTT | 4.6 | 18 | 130 | 94 | 90 | 91 |
| 1,3DBA5OTT | 3.0 | 14 | — | 58 | — | 92 |
| 1,3DAP5TTOT | 3.0 | 14 | — | 48 | — | 72 |
| 1,3DEA5HTT | 3.3 | 13 | — | 61 | — | 91 |

Industrial Applicability

The compounds of the present invention have utility as antiozonants in rubber compositions to protect the compositions from the degradative effects of ozone. The rubber compositions of the present invention have utility in articles such as tires, belts, hoses and other rubber goods particularly where those articles may be exposed to the degradative effects of ozone. A particularly beneficial property is the non-staining characteristic of those rubber compositions containing structures wherein the radicals are selected from groups free of para-phenylenediamine moieties. However, even those compositions containing structures having para-phenylenediamine, while they may not be as non-staining as some of the other embodiments of the invention, are lighter colored than the conventional para-phenylenediamines such as Wingstay TM 300 and may migrate to a much lesser degree. These would have applicability to light colored rubber compositions such as white sidewalls, shoe products, floor mats and the like.

While certain representative embodiments and details have been shown for the purpose of illustrating the invention, it will be apparent to those skilled in this art that various changes and modifications may be made therein without departing from the scope of the invention.

What is claimed is:

1. A rubber composition comprising a non-halogenated rubber susceptible to ozone degradation and an antiozonant effective amount of a compound represented by the following structural formula:

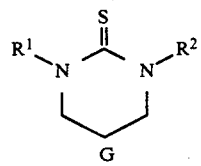

wherein G is →N—$R^3$;
wherein $R^1$, $R^2$ and $R^3$ are independently selected from the group consisting of
(a) alkyl radicals having 1 to 25 carbon atoms, wherein said alkyl may be substituted by an amino group,
(b) cycloalkyl radicals having 3 to 25 carbon atoms, wherein said cycloalkyl may be substituted by an amino group,
(c) aryl radicals having 6 to 25 carbon atoms; and
(d) radicals selected from the group consisting of those radicals represented by the following structural formulae:

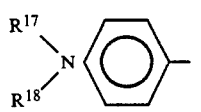

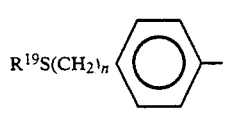

and

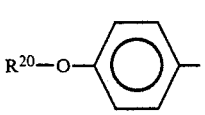

wherein $R^{17}$, $R^{18}$, $R^{19}$ and $R^{20}$ are independently selected from the group consisting of hydrogen; alkyl radicals having 1 to 25 carbon atoms; and aryl radicals having 6 to 25 carbon atoms; n is an integer of 1 to 6;
wherein $R^3$ can also be hydrogen;
wherein when a radical from member (a) or (b) is substituted with an amino group, the alpha atom of the radical is free of amino groups.

2. A rubber composition comprising a non-halogenated rubber and a compound represented by the following structure:

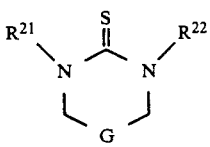

wherein G is →N—$R^{23}$;
wherein $R^{21}$, $R^{22}$ and $R^{23}$ are independently selected from the group consisting of
(a) alkyl radicals having 1 to 25 carbon atoms, wherein said alkyl may be substituted by an amino group, (b) cycloalkyl radicals having 3 to 25 carbon atoms, wherein said cycloalkyl may be substituted by an amino group,
(c) aryl radicals having 6 to 25 carbon atoms, and
(e) radicals selected from the group consisting of those radicals represented by the following structural formulae:

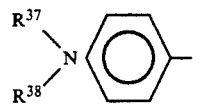 (D)

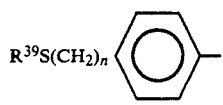 (E)

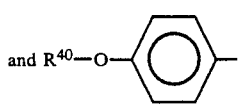 (F)

wherein $R^{37}$, $R^{38}$, $R^{39}$ and $R^{40}$ are independently selected from the group consisting of hydrogen; alkyl radicals having 1 to 25 carbon atoms; and aryl radicals having 6 to 25 carbon atoms; n is an integer of 1 to 6;
wherein when a radical from member (a) or (b) is substituted with an amino group, the alpha atom of the radical is free of amino groups; $R^{23}$ can also be hydrogen.

3. A composition of matter represented by the following structural formula:

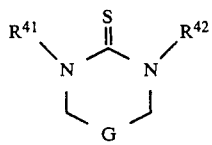 (XI)

wherein G is —N—$R^{43}$;
wherein $R^{41}$, $R^{42}$ and $R^{43}$ are independently selected from the group consisting of
(a) alkyl radicals having 1 to 25 carbon atoms, wherein said alkyl may be substituted by an amino group,
(b) cycloalkyl radicals having 3 to 25 carbon atoms, wherein said cycloalkyl may be substituted by an amino group,
(c) aryl radicals having 6 to 25 carbon atoms, and
(e) radicals selected from the group consisting of those radicals represented by the following structural formulae:

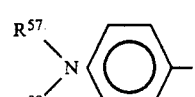 (H)

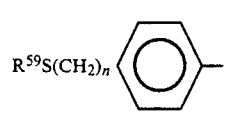 (J)

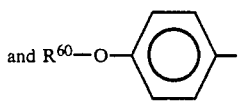 (K)

wherein $R^{57}$, $R^{58}$, $R^{59}$ and $R^{60}$ are independently selected from the group consisting of hydrogen; alkyl radicals having 1 to 25 carbon atoms; and aryl radicals having 6 to 25 carbon atoms; n is an integer of 1 to 6;
wherein when a radical from member (a) or (b) is substituted with an amino group, the alpha atom of the radical is free of amino groups;
wherein at least one of $R^{41}$, $R^{42}$ and $R^{43}$ is selected from the radicals of member (f).

4. The rubber composition of claim 1 having therein an antiozonant effective amount of tetrahydro-5-(t)-butyl-1,3-di-n-butyl-(S)-triazine thione.

5. The rubber composition of claim 1 having therein an antiozonant effective amount of tetrahydro-5-cyclohexyl-1,3-di-n-butyl-(S)-triazine thione.

6. The rubber composition of claim 1 having therein an antiozonant effective amount of tetrahydro-5-cyclohexyl-1,3-diethyl-(S)-triazine thione.

7. The rubber composition of claim 1 having therein an antiozonant effective amount of tetrahydro-1,3-di-(4-anilinophenyl)-5-butyl-(S)-triazine thione.

8. The rubber composition of claim 1 having therein an antiozonant effective amount of tetrahydro-1,3-di-(4-anilinophenyl)-5-(t)-octyl-(S)-triazine thione.

9. The rubber composition of claim 1 having therein an antiozonant effective amount of 1,3-di-(4-isopropylaminophenyl)-5-butyl-(S)-triazine thione.

10. The rubber composition of claim 1 having therein an antiozonant effective amount of 1,3-di-(4-isopropylaminophenyl)-5-t-octyl-(S)-triazine thione.

11. The rubber composition of claim 1 having therein an antiozonant effective amount of tetrahydro-1,3,5-tributyl-(S)-triazine thione.

12. The rubber composition of claim 1 having therein an antiozonant effective amount of tetrahydro-1,3-bis-[4-(1,3-dimethylbutylamino)-phenyl]-5-octyl-(S)-triazine thione.

13. The rubber composition of claim 2 wherein said compound is tetrahydro-5-(t)-butyl-1,3-di-n-butyl-(S)-triazine thione.

14. The rubber composition of claim 2 wherein said compound is tetrahydro-5-cyclohexyl-1,3-di-n-butyl-(S)-triazine thione.

15. The rubber composition of claim 2 wherein said compound is tetrahydro-5-cyclohexyl-1,3-diethyl-(S)-triazine thione.

16. The rubber composition of claim 2 wherein said compound is tetrahydro-1,3-di-(4-anilinophenyl)-5-butyl-(S)-triazine thione.

17. The rubber composition of claim 2 wherein said compound is tetrahydro-1,3-di-(4-anilinophenyl)-5-t-octyl-(S)-triazine thione.

18. The rubber composition of claim 2 wherein said compound is 1,3-di-(4-isopropylaminophenyl)-5-butyl-(S)-triazine thione.

19. The rubber composition of claim 2 wherein said compound is 1,3-di-(4-isopropylaminophenyl)-5-t-octyl-(S)-triazine thione.

20. The rubber composition of claim 2 wherein said compound is tetrahydro-1,3,5-tributyl-(S)-triazine thione.

21. The composition of matter of claim 2 wherein said compound is tetrahydro-1,3-bis-[4-(1,3-dimethylbutylamino)-phenyl]-5-octyl-(S)-triazine thione.

22. The composition of matter of claim 3 wherein said compound is tetrahydro-1,3-bis-(4-dimethylaminophenyl)-5-butyl-(S)-triazine thione.

23. The composition of matter of claim 3 wherein said compound is tetrahydro-1,3-bis-(4-dimethylaminophenyl)-5-t-octyl-(S)-triazine thione.

24. The composition of matter of claim 3 wherein said compound is tetrahydro-1,3-di-(4-anilinophenyl)-5-butyl-(S)-triazine thione.

25. The composition of matter of claim 3 wherein said compound is tetrahydro-1,3-di-(4-anilinophenyl)-5-t-octyl-(S)-triazine thione.

26. The composition of matter of claim 3 wherein said compound is tetrahydro-1,3-di-(4-isopropylaminophenyl)-5-butyl-(S)-triazine thione.

27. The composition of matter of claim 3 wherein said compound is tetrahydro-1,3-di-(4-isopropylaminophenyl)-5-t-octyl-(S)-triazine thione.

28. The composition of matter of claim 3 wherein said compound is tetrahydro-1,3-bis-[4-(1,3-dimethylbutylamino)phenyl]-5-octyl-(S)-triazine thione.

* * * * *